United States Patent [19]

Darko et al.

[11] 4,429,141
[45] Jan. 31, 1984

[54] PHYSIOLOGICALLY ACTIVE COMPOUNDS AND THEIR ISOLATION

[75] Inventors: Laszlo L. Darko, Redding, Conn.;
Koji Nakanishi, New York, N.Y.;
Masachi Nakagawa, Osaka, Japan

[73] Assignee: Richter Gedeon Vegyeszeti Gyar R.T., Budapest, Hungary

[21] Appl. No.: 357,805

[22] Filed: Mar. 15, 1982

[51] Int. Cl.$^3$ .......................................... C07D 311/78
[52] U.S. Cl. ................................................. 549/382
[58] Field of Search ...................................... 549/382

[56] References Cited

PUBLICATIONS

Chemical Abstracts 75:45669q (1971).
Chemical Abstracts 87:39332f (1977).
Chemical Abstracts 89:109164u (1978).
Chemical Abstracts 98:50322a (1983).
Chemical Abstracts 95:203790s (1981).
Chemical Abstracts 98:89040g (1983).

*Primary Examiner*—Ethel G. Love
*Attorney, Agent, or Firm*—Thomas E. Spath

[57] ABSTRACT

Physiologically active crystalline products of manufacture having the formulas: t,0010
are described. These compounds are effective against the toxic venoms of poisonous snakes, spiders and other insects, and against *E. coli* endotoxins; methods are described for isolation of the above compounds.

7 Claims, No Drawings

PHYSIOLOGICALLY ACTIVE COMPOUNDS AND THEIR ISOLATION

BACKGROUND OF THE INVENTION

1. Field of the Invention

This invention relates to products of manufacture which are substantially pure crystalline pterocarpan compounds which have been isolated from the crude extracts of natural products and to methods for isolating the compounds.

2. Description of the Prior Art

It has been known that the aqeuous alcoholic extract of the root of the South American *cabeca de negra* tree has been available to plantation workers in the upper Amazon jungle as an oral antidote against snake and spider venoms. About ten varieties of the species *cabeca de negra* are known in South America. Neither the nature of the active components nor studies on the side effects, pharmacological activity, stability and the like are known to have been published on the compounds of the invention. Pterocarpans possessing antimicrobial properties have been identified in the literature, see *Heterocycles*, Vol. 15, 1163 (1981).

SUMMARY OF THE INVENTION

The invention includes the following products of manufacture which have been isolated in substantially pure crystalline form:

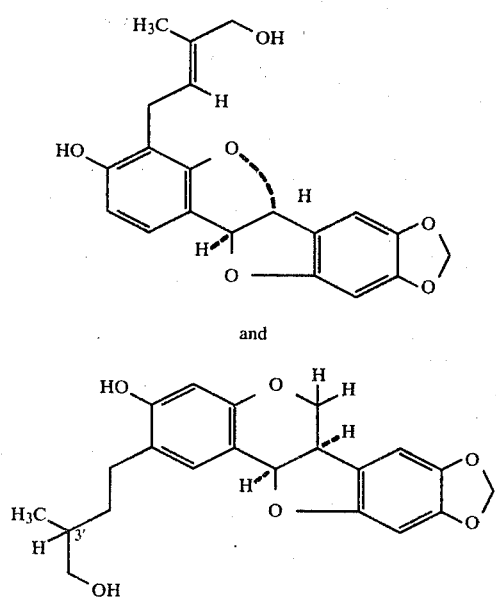

For convenience, the compounds of the above structure will be referred to hereinafter as cabenegrin I and cabenegrin II, or as compounds (I) and (II), respectively. The invention also includes the step-wise method employed to recover and isolate the essentially pure crystalline products referred to as cabenegrin I and cabenegrin II.

The compounds cabenegrin I and cabenegrin II have pharmaceutical utility in the treatment of mammals, including man, that have been envenomated by poisonous snakes and insects. That is, these compounds act as potent antidotes against effects of snake and insect toxins. The compounds (I) and (II) are also useful in treating the effects of other known organic toxins such as *E. coli* endotoxin and that produced by *Clostridium botulinum*, commonly referred to as botulism or food poisoning. The details of tests establishing the utility of compounds I and II are described in a co-pending application filed concurrently herewith in the name of Lazslo Darko under U.S. Ser. No. 358,191, and the entire disclosure of that application is incorporated herein by reference. Pharmaceutical utility is generally indicated for the treatment of the effects in mammals of toxins produced by pathogenic bacteria (endotoxins and exotoxins) which attack the nervous system of the victim and particularly where paralysis of the respiratory system is manifested. Treatment against the effects of cardio-vascular toxins is also indicated.

The compounds can be administered orally in liquid form as a suspension or solubilized in a compatible pharmaceutical carrier. The pure crystalline material can be administered orally in capsule or tablet form when compounded with suitable pharmaceutical carriers. Alternatively, either of the compounds cabenegrin I or II can be dissolved in a suitable liquid pharmaceutical carrier and the solution administered intravenously by syringe, or by catheter where monitoring equipment is available to determine the effects of the therapy. If desired compounds (I) and (II) can be mixed together in various proportions, and the mixture prepared as described above with suitable pharmaceutical carriers.

DETAILED DESCRIPTION OF THE INVENTION

Approximately ½ kilo of the washed root of the *cabeca de negra* tree is chopped into small pieces which may then be mascerated, pulverized or otherwise treated to break down the fibrous structure. This step can be accomplished in a blender or laboratory homogenizer. Roots evidencing mold or fungus should not be used. The pulverized root is placed in a large glass beaker or other suitable vessel which may be covered and subsequently stirred. A sufficient quantity of ethanol:water 77:23 is added to cover the pulverized root and briskly stirred for a few minutes. The vessel containing the aqueous ethanol and root is allowed to stand at ambient temperatures for at least 48 hours, with occasional stirring. At the end of this period, the aqueous alcoholic solution comprising the crude extract is separated from the root by any convenient means, for example, by pouring through medium filter paper. The pulverized root is discarded. The filtered solution is the color of strong tea.

The following procedure was employed to isolate the active compounds from the crude extract as prepared above.

The aqueous ethanol crude extract (135 ml) was concentrated by gentle warming under vacuum to obtain 1.2 grams of a brown oily residue. This concentrated material was treated with 50% aqueous methanol and the solution was extracted by vigorous shaking with hexane. The hexane layer was separated and discarded. The water layer was extracted with ether by vigorous shaking. The ether layer and the water layer were separated, the ether layer (640 milligrams) being set aside. The water layer was extracted with n-butyl alcohol by vigorous shaking. The n-butyl alcohol layer was separated and set aside, and the water layer was discarded.

The ether layer extracted above is subjected to high pressure liquid chromatography (HPLC) on Sephadex LH-20 as a first step and as the next step on silica gel using aqueous methanol as the eluting solvent. This procedure results in two fractions, and the first is further separated by HPLC employing Partisil-10 eluted with 3% methanol in methylene chloride to yield pure solid compounds.

The compound identified as cabenegrin I is recovered as a white crystalline material in a yield of 44 mg. A sharp melting point of 167°–168° C. is obtained and analysis shows the composition to be $C_{21}H_{20}O_6$. The Rf value of compound I on thin layer chromatography employing silica gel CO/Kiesel guhr F-254 and benzene/ethyl acetate/methanol (15/4/1) was 0.53.

The U.V., C.D., and I.R. of compound I are as follows:

UV (in MeOH): 209 nm (E 75,000), 233 nm (shoulder, E 24,000), 309 nm (E 13,000)

CD (in MeOH): 213 nm (E −25.58), 220 nm (ΔE −2.00), 238 nm (ΔE −9.84); 302 (ΔE +3.15)

IR (in CHCl3): 3550 cm$^{-1}$, 1600 cm$^{-1}$, 1113 cm$^{-1}$, 925 cm$^{-1}$.

In addition to these spectral data, the following $^1$H-NMR, $^{13}$C-NMR, and MS (EI) data were measured; these spectroscopic measurements led to the depicted structure.

PMR, CMR and MS of Compound (I):

Cabenegrin I
$C_{21}H_{20}O_6$

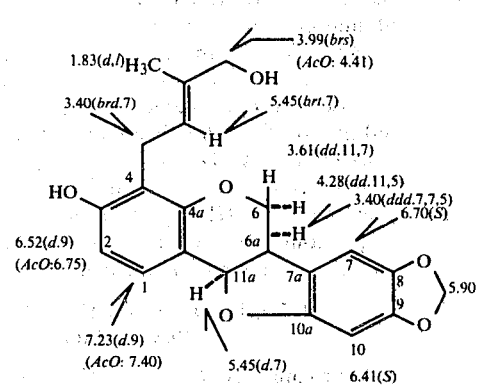
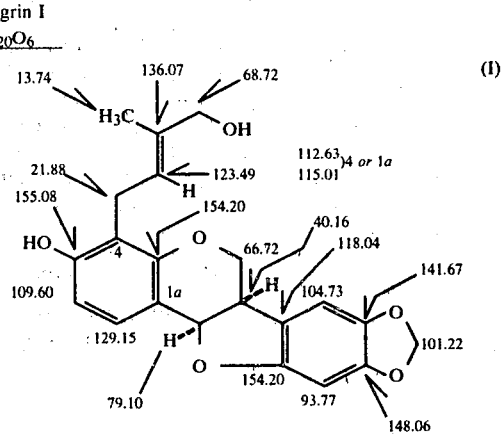

(I)

EI(18eV)
368(M$^+$, 50%)
350(M$^+$—H$_2$O, 100%)
335(M$^+$—H$_2$O—Me, 95%)

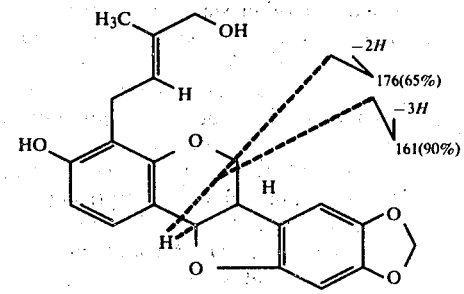

−2H
176(65%)
−3H
161(90%)

The second sample of material recovered from the HPLC described above comprised an oily mixture of approximately 10 mg. This second active fraction, which had been obtained from the HPLC of the ether layer described above, is treated as follows to obtain the compound cabenegrin II. The mixture was subjected to further HPLC employing μ-Bondapak C18 and methanol/acetonitrile/H$_2$O/n-PrOH (71/71/59/2). Compound (II) was obtained in essentially pure crystalline form in a yield of about 1 mg. The structure of this compound is based on the following physical constants:

Cabenegrin II
$C_{21}H_{22}O_6$ (EI-MS)

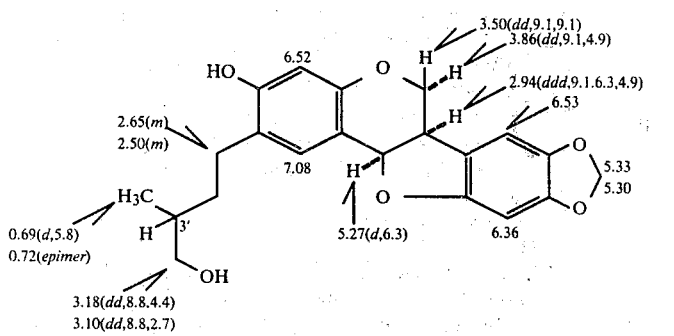

UV(MeOH): 204 nm(ε116,000)     CD(MeOH): 237 nm(Δε−6.68)
         230 nm(ε8,000)                  280 nm(Δε−0.46)
         292 nm(ε9,400)                  299 nm(Δε+1.72)
         308 nm(ε11,800)

The structure of compound (II) is shown by NMR data to be a 3:1 mixture of epimers at C-3'. The structures of both compounds cabenegrin I and cabenegrin II have been confirmed by synthesis of their respective racemates.

What is claimed is:

1. A substantially pure crystalline compound having a melting point of 167°–168° C. and the following structure:

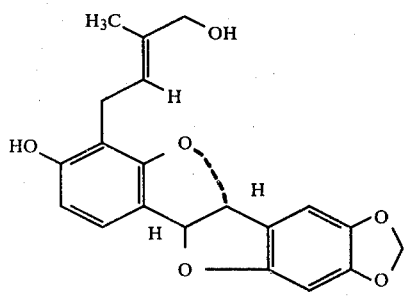

2. A compound of the structure

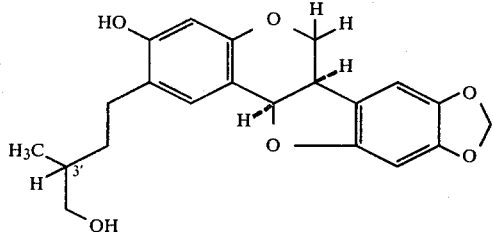

3. A mixture of compounds having the structure

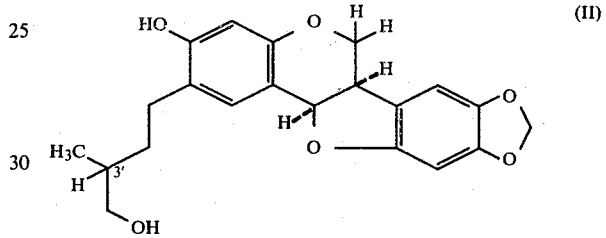

which comprises a 3:1 mixture of epimers at C-3'.

4. A method of manufacturing substantially pure crystalline compound having a melting point of 167°–168° C. of the structure:

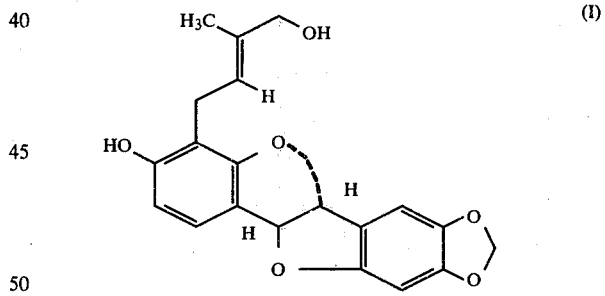

which method comprises the steps of
(a) preparing a crude aqueous alcoholic extract from the comminuted root of the *cabeca de negra* tree;
(b) concentrating the crude extract to an oily residue;
(c) treating said oily residue with aqueous methanol and thereafter extracting with hexane;
(d) extracting the aqueous layer resulting from step (c) with ether;
(e) subjecting the ether layer resulting from step (d) to high pressure liquid chromatography employing an eluting solution comprising methanol;
(f) separating a first fraction and a second fraction; and
(g) recovering from said first fraction compound (I).

5. The method of claim 4, which comprises subjecting the first fraction obtained in step (f) to high pressure liquid chromatography employing an eluting solution comprising methanol and methylene chloride to obtain compound (I).

6. A method of manufacturing a compound of the structure

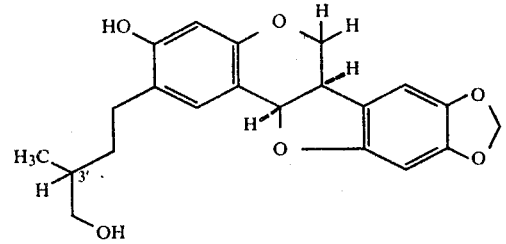

(II)

which method comprises the steps of (a) preparing a crude aqueous alcoholic extract from the comminuted root of the *cabeca de negra* tree;
(b) concentrating the crude extract to an oily residue;
(c) treating said oily residue with aqueous methanol and thereafter extracting with hexane;
(d) extracting the aqueous layer resulting from step (c) with ether;
(e) subjecting the ether layer resulting from step (d) to high pressure liquid chromatography employing an eluting solution comprising methanol;
(f) separating a first fraction and a second fraction; and
(g) recovering from said second fraction compound (II).

7. The method of claim 6, which comprises subjecting the second fraction obtained in step (f) to high pressure liquid chromatography employing an eluting solution comprising methanol, acetonitrite, water and n-PrOH to obtain compound (II).

* * * * *